United States Patent
Lev et al.

(10) Patent No.: US 11,642,085 B2
(45) Date of Patent: May 9, 2023

(54) AUTOMATED HEALTH CHECK DEVICE AND METHODS

(71) Applicant: NEC Corporation Of America, Herzlia (IL)

(72) Inventors: Tsvi Lev, Tel-Aviv (IL); Yaacov Hoch, Ramat-Gan (IL)

(73) Assignee: NEC Corporation Of America, Herzlia (IL)

( * ) Notice: Subject to any disclaimer, the term of this patent is extended or adjusted under 35 U.S.C. 154(b) by 428 days.

(21) Appl. No.: 17/063,811

(22) Filed: Oct. 6, 2020

(65) Prior Publication Data

US 2022/0104771 A1    Apr. 7, 2022

(51) Int. Cl.
| | |
|---|---|
| A61B 5/00 | (2006.01) |
| A61B 5/01 | (2006.01) |
| B60R 11/04 | (2006.01) |
| B60N 2/00 | (2006.01) |
| G16H 50/30 | (2018.01) |
| G16H 40/67 | (2018.01) |
| A61B 5/0205 | (2006.01) |
| A61B 5/024 | (2006.01) |
| A61B 5/05 | (2021.01) |

(Continued)

(52) U.S. Cl.
CPC .......... *A61B 5/6887* (2013.01); *A61B 5/0077* (2013.01); *A61B 5/015* (2013.01); *A61B 5/02055* (2013.01); *B60N 2/002* (2013.01); *B60R 11/04* (2013.01); *G16H 40/67* (2018.01); *G16H 50/30* (2018.01); *A61B 5/02405* (2013.01); *A61B 5/05* (2013.01); *A61B 5/0816* (2013.01); *A61B 5/0823* (2013.01); *A61B 5/14542* (2013.01); *A61B 8/5261* (2013.01); *A61B 2562/0204* (2013.01)

(58) Field of Classification Search
CPC ..... A61B 5/6887; A61B 5/0077; A61B 5/015; A61B 5/02055; A61B 5/02405; A61B 5/05; A61B 5/0816; A61B 5/0823; A61B 5/14542; A61B 8/5261; A61B 2562/0204; B60N 2/002; B60R 11/04; G16H 40/67; G16H 50/30
USPC ..................................................... 340/576
See application file for complete search history.

(56) References Cited

U.S. PATENT DOCUMENTS

| | | | |
|---|---|---|---|
| 2014/0099028 A1* | 4/2014 | Shirron ................. | G06F 40/174 382/181 |
| 2020/0064444 A1* | 2/2020 | Regani .................. | G01S 13/931 |

(Continued)

FOREIGN PATENT DOCUMENTS

WO    WO-2022258560 A1 * 12/2022

*Primary Examiner* — Omar Casillashernandez

(57) ABSTRACT

An automated health check device and methods, the device comprising: at least one imaging sensor configured for capturing at least one image of at least an area confined by a window of the vehicle; at least one vital signs sensor configured for measuring a health parameter of a passenger at the area confined by the window; and at least one processor configured for: acquiring and analyzing the at least one image to determine location of the window; determining based on the determined location of the window a location of the passenger; determining the at least one vital signs sensor being oriented to a predetermined point of view in relation to the location of the passenger determined; and obtaining a measurement of the health parameter of the passenger from the at least one vital signs sensor.

37 Claims, 8 Drawing Sheets

(51) Int. Cl.
  *A61B 5/08*   (2006.01)
  *A61B 5/145*  (2006.01)
  *A61B 8/08*   (2006.01)

(56) References Cited

U.S. PATENT DOCUMENTS

| | | | |
|---|---|---|---|
| 2020/0269688 A1* | 8/2020 | Dagley | H04W 4/70 |
| 2020/0309932 A1* | 10/2020 | Zeng | H01Q 1/3241 |
| 2020/0348406 A1* | 11/2020 | Jain | G05D 1/028 |
| 2020/0359913 A1* | 11/2020 | Ghodrati | A61B 5/1117 |
| 2022/0028556 A1* | 1/2022 | Tiwari | G16H 50/30 |
| 2023/0014426 A1* | 1/2023 | Guidi | B60R 11/04 |

\* cited by examiner

AUTOMATED HEALTH CHECK DEVICE AND METHODS

FIELD AND BACKGROUND OF THE INVENTION

The present invention, in some embodiments thereof, relates to remote sensing and, more specifically, but not exclusively, to automated health check device and methods.

Viral infections that can spread throughout the general population via exposure of the healthy to infected individuals or even spaces or objects contaminated thereby, due to which the former may contract the virus from the latter and further become carriers thereof and infect others in turn, are of great concern not only among public health experts and epidemiologists, but also to government officials and organizations as well as the humanity at large, especially in face of dangerous and potentially lethal strains and global outbreaks.

Small confined areas, limited airflow or closed-loop ventilation, crowdedness, poor hygiene or sanitary conditions and the like are among factors well-recognized as significantly increasing risk of contracting and spreading of infections and viral diseases. A critical step on course to containment of morbidity rates and cutting infection chains off is thus by an early detection and isolation of infected individuals from healthy ones, preferably prior to any mixing of the two populations together can be expected to occur at high likelihood, such as for example by employing access control at doorways or pathways to and/or from places and regions where one or more of these risk factors are present and pose greater threat of infection hazard.

Screening of entrants at a doorway or of passing bystanders along a pathway to locations of peak or steady highly concentrated population can be performed to identify potential carriers or infected individuals and take protective measures such as denying access, reporting to health or enforcement authorities, and the like. For example, the screening process may entail questioning, e.g. regarding health condition in general and suspect symptoms experienced in particular, recent hazardous exposure risks, etc.; performance of measurement of one or more health parameters, e.g. measuring body temperature with a thermometer; or a combination of both.

SUMMARY OF THE INVENTION

It is an object of the present invention to provide a device and method for automated health check of passengers of a vehicle.

The foregoing and other objects are achieved by the features of the independent claims. Further implementation forms are apparent from the dependent claims, the description and the figures.

According to an aspect of some embodiments of the present invention there is provided a device for automated health check of passengers of a vehicle, comprising: at least one imaging sensor configured for capturing at least one image of at least an area confined by a window of the vehicle; at least one vital signs sensor configured for measuring a health parameter of a passenger at the area confined by the window; and at least one processor configured for: acquiring and analyzing the at least one image to determine location of the window; determining based on the determined location of the window a location of the passenger; determining the at least one vital signs sensor being oriented to a predetermined point of view in relation to the location of the passenger determined; and obtaining a measurement of the health parameter of the passenger from the at least one vital signs sensor.

Optionally, the device further comprising at least one mechanical assembly configured for reorienting the at least one vital signs sensor, wherein the at least one processor being further configured for instructing the at least one mechanical assembly to reorient the at least one vital signs sensor to the predetermined point of view.

Optionally, the at least one vital signs sensor comprising an electronically steerable radar, wherein the at least one processor being further configured for reorienting the electronically steerable radar to the predetermined point of view.

Optionally, the device further comprising a user interface for providing output, wherein the at least one processor being further configured for providing via the user interface instructions to the passenger to move at least a body portion for placing the at least one vital signs sensor in orientation to the predetermined point of view.

Optionally, the at least one imaging sensor comprising at least one spatial sensor configured for obtaining depth data of at least the area confined by the window, wherein the at least one processor being further configured for analyzing the depth data to determine whether the window being in a rolled down position allowing clear line-of-sight between the at least one vital signs sensor and the passenger.

Optionally, the device further comprising a user interface for providing output, wherein the at least one processor being further configured for: prior to obtaining the measurement and responsive to determination that the window being in position not allowing clear line-of-sight between the at least one vital signs sensor and the passenger, providing via the user interface instructions to an operator of the vehicle to roll and maintain the window down for duration of the measurement.

Optionally, the device further comprising a user interface for providing output, wherein the at least one processor being further configured for: prior to obtaining the measurement and responsive to determination that the location of the window exceeding a predetermined threshold distance in relation to the at least one vital signs sensor, determining a corrective translation of the vehicle relocating the window within the predetermined threshold distance, and providing via the user interface instructions to an operator of the vehicle for effecting the corrective translation.

Optionally, the at least one imaging sensor comprising at least one thermal sensor configured for obtaining temperature data of at least the area confined by the window, wherein the at least one processor being further configured for analyzing the temperature data to determine whether thermal conditions in the vehicle enable proper functioning of the at least one vital signs sensor.

Optionally, the at least one processor being further configured for determining and effecting calibration of the at least one vital signs sensor in mitigation of thermal conditions in the vehicle.

Optionally, the device further comprising a user interface for providing output, wherein the at least one processor being further configured for outputting via the user interface instructions to the passenger to perform at least one of extending a predetermined body portion out of the window and making accessible a predetermined inner cavity portion at a body orifice in mitigation of thermal conditions in the vehicle.

Optionally, the at least one imaging sensor comprising at least one thermal sensor configured for obtaining temperature data of at least the area confined by the window, wherein the at least one processor being further configured for analyzing the temperature data to recognize a pattern indicating usage of a climate control system of the vehicle.

Optionally, the at least one processor being further configured for determining and effecting calibration of the at least one vital signs sensor in compensation of a difference in the measurement of the health parameter caused by usage of the climate control system.

Optionally, the device further comprising a user interface for providing output, wherein the at least one processor being further configured for outputting via the user interface instructions to the passenger to perform at least one of extending a predetermined body portion out of the window and making accessible a predetermined inner cavity portion at a body orifice in override of disruptive impact on the measurement of the health parameter caused by usage of the climate control system.

Optionally, the at least one processor being further configured for: analyzing the at least one image to determine a vibration frequency of the vehicle; and removing the vibration frequency from the measurement obtained by the at least one vital signs sensor.

Optionally, the device further comprising a user interface for providing output, wherein the at least one processor being further configured for: analyzing the at least one image to determine a vibration frequency of the vehicle; and, responsive to determination that the vibration frequency exceeding a predetermined threshold, outputting via the user interface instructions to an operator of the vehicle to turn and maintain off the vehicle's engine for duration of the measurement.

Optionally, the device further comprising a user interface for providing output, wherein the at least one processor being further configured for analyzing the at least one image to determine at least one of location and velocity of the vehicle and outputting via the user interface instructions to an operator of the vehicle to limit velocity and to halt the vehicle at a predetermined location.

Optionally, the at least one imaging sensor and the at least one vital signs sensor comprising at least one sensor selected from the group consisting of: a video camera; a thermal camera; a depth camera; an ultra-wideband radar; a laser speckle imaging device; a microphone; an ultrasonic sensor; a radiance sensor; and a laser Doppler vibrometer.

Optionally, the health parameter being selected from the group consisting of: a body temperature; a breathing rate; a breathing depth; a heart rate; a heart rate stability; cough presence; a blood oxygenation level; and a voice-indicated nasal congestion and/or throat irritation.

Optionally, the at least one processor being further configured for analyzing the at least one image to determine at least one personal parameter of the passenger selected from the group consisting of: age; gender; weight; height; and facial recognition.

Optionally, the at least one processor being further configured for: performing analysis of and extracting from the at least one image a unique identifier of the vehicle; and providing an output associating the unique identifier with the measurement obtained for each passenger of the vehicle.

According to an aspect of some embodiments of the present invention there is provided a method for automated health check of passengers of a vehicle, comprising: acquiring from at least one imaging sensor at least one image of at least an area confined by a window of the vehicle; analyzing the at least one image to determine location of the window; determining based on the determined location of the window a location of a passenger; determining at least one vital signs sensor being oriented to a predetermined point of view in relation to the location of the passenger determined; and obtaining a measurement of a health parameter of the passenger from the at least one vital signs sensor.

Optionally, the method further comprising reorienting the at least one vital signs sensor to the predetermined point of view by at least one of a mechanical reorienting means and an electronical reorienting means.

Optionally, the method further comprising instructing the passenger to move at least a body portion for placing the at least one vital signs sensor in orientation to the predetermined point of view.

Optionally, the method further comprising: obtaining depth data of at least the area confined by the window from at least one spatial sensor comprised in the at least one imaging sensor; and analyzing the depth data to determine whether the window being in a rolled down position allowing clear line-of-sight between the at least one vital signs sensor and the passenger.

Optionally, the method further comprising: prior to obtaining the measurement and responsive to determination that the window being in position not allowing clear line-of-sight between the at least one vital signs sensor and the passenger, providing instructions to an operator of the vehicle to roll and maintain the window down for duration of the measurement.

Optionally, the method further comprising: prior to obtaining the measurement and responsive to determination that the location of the window exceeding a predetermined threshold distance in relation to the at least one vital signs sensor, determining a corrective translation of the vehicle relocating the window within the predetermined threshold distance; and providing instructions to an operator of the vehicle for effecting the corrective translation.

Optionally, the method further comprising: obtaining temperature data of at least the area confined by the window from at least one thermal sensor comprised in the at least one imaging sensor, and analyzing the temperature data to determine whether thermal conditions in the vehicle enable proper functioning of the at least one vital signs sensor.

Optionally, the method further comprising determining and effecting calibration of the at least one vital signs sensor in mitigation of thermal conditions in the vehicle.

Optionally, the method further comprising outputting instructions to the passenger to perform at least one of extending a predetermined body portion out of the window and making accessible a predetermined inner cavity portion at a body orifice in mitigation of thermal conditions in the vehicle.

Optionally, the method further comprising: obtaining temperature data of at least the area confined by the window from at least one thermal sensor comprised in the at least one imaging sensor, and analyzing the temperature data to recognize a pattern indicating usage of a climate control system of the vehicle.

Optionally, the method further comprising: determining and effecting calibration of the at least one vital signs sensor in compensation of a difference in the measurement of the health parameter caused by usage of the climate control system.

Optionally, the method further comprising: outputting instructions to the passenger to perform at least one of extending a predetermined body portion out of the window and making accessible a predetermined inner cavity portion at a body orifice in override of disruptive impact on the measurement of the health parameter caused by usage of the climate control system.

Optionally, the method further comprising analyzing the at least one image to determine a vibration frequency of the vehicle; and removing the vibration frequency from the measurement obtained by the at least one vital signs sensor.

Optionally, the method further comprising: analyzing the at least one image to determine a vibration frequency of the vehicle; and, responsive to determination that the vibration frequency exceeding a predetermined threshold, outputting instructions to an operator of the vehicle to turn and maintain off the vehicle's engine for duration of the measurement.

Optionally, the method further comprising: analyzing the at least one image to determine at least one of location and velocity of the vehicle, and outputting instructions to an operator of the vehicle to limit velocity and to halt the vehicle at a predetermined location.

Optionally, the method further comprising analyzing the at least one image to determine at least one personal parameter of the passenger selected from the group consisting of: age; gender; weight; height; and facial recognition.

Optionally, the method further comprising: performing analysis of and extracting from the at least one image a unique identifier of the vehicle; and providing an output associating the unique identifier with the measurement obtained for each passenger of the vehicle.

According to an aspect of some embodiments of the present invention there is provided a method for automated health check of passengers of a vehicle, comprising: acquiring from at least one imaging sensor at least one image of at least a cabin area of the vehicle occupying one or more passengers; analyzing the at least one image to determine distinct location of each of the one or more passengers along a longitudinal axis of the vehicle; determining, based on distinct location of each of the one or more passengers determined and a configuration of a plurality of vital signs sensors deployed at predetermined locations, one or more halting points of the vehicle for obtaining a measurement of a health parameter of each of the one or more passengers by the plurality of vital signs sensors; and providing instructions to an operator of the vehicle to successively mobilize the vehicle to each of the one or more halting points and maintain position of the vehicle therein for duration of the measurement.

According to an aspect of some embodiments of the present invention there is provided a method for automated health check of passengers of a vehicle, comprising: acquiring from at least one imaging sensor at least one image of a cabin area portion of the vehicle, wherein the at least one image capturing at least a face of a passenger; analyzing the at least one image to determine location of the passenger, the analyzing comprising applying face recognition analysis on the at least one image; determining at least one vital signs sensor being oriented to a predetermined point of view in relation to the location of the passenger determined; obtaining a measurement of a health parameter of the passenger from the at least one vital signs sensor; and analyzing the measurement to determine non-fraudulent representation of the passenger in the at least one image.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
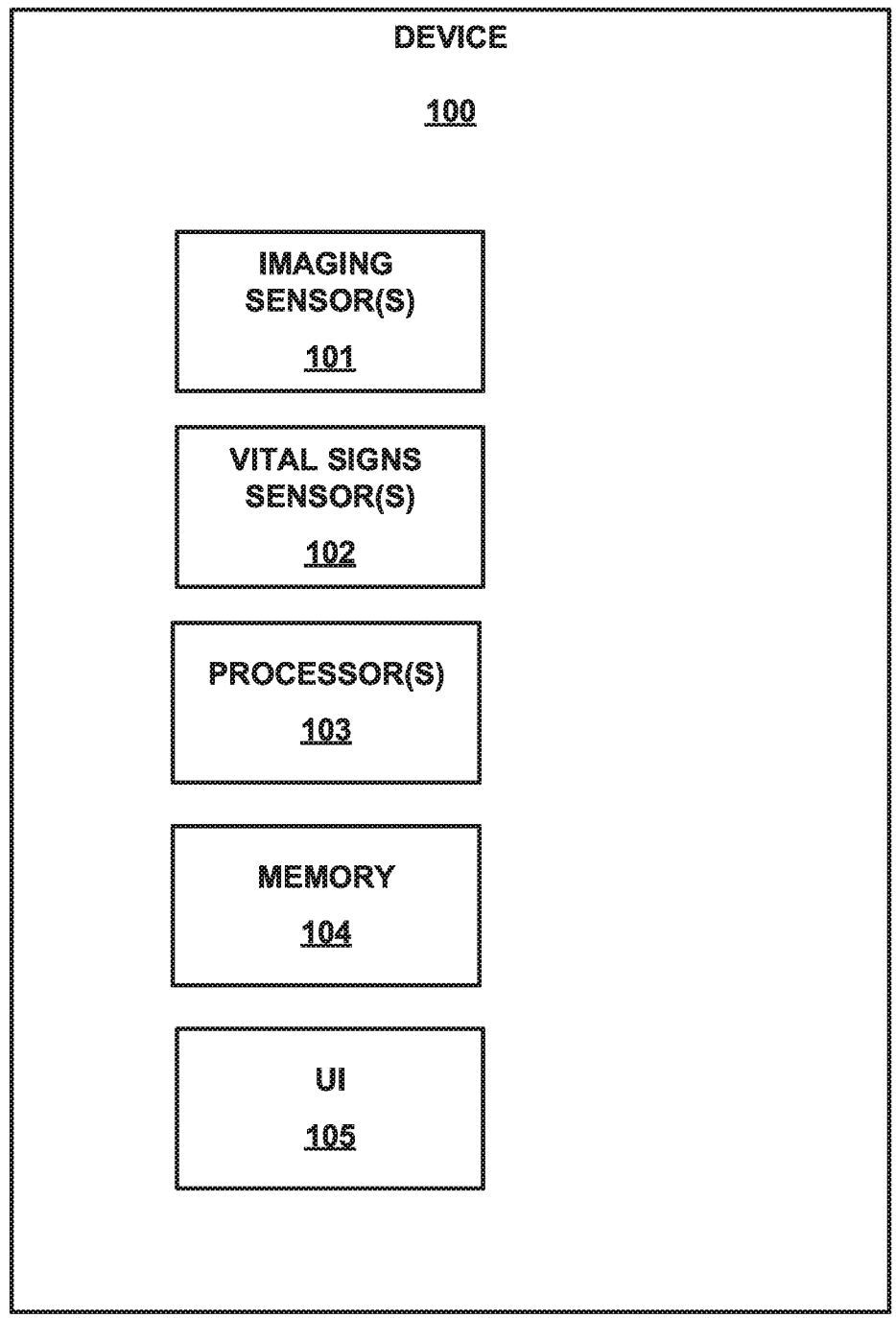
FIG. 1 is a block diagram of a device for automated health check of passengers of a vehicle, in accordance with some embodiments of the present invention.

The present invention, in some embodiments thereof, relates to remote sensing and, more specifically, but not exclusively, to automated health check device and methods.

Screening incomers at entries into densely populated spaces and/or settlements may be key in containment and prevention of viral infections spread. However, when performed manually, such procedure may suffer from major disadvantages, one of which being heightened exposure of teams tasked with the manual screening to a risk of contracting the viral infection and spreading it themselves. Such teams may also require use of protective gear and clothing, most of which being disposable and frequently replaced, thus resulting in excessive amounts of waste that is in itself biological hazardous. Another drawback of manual screening is susceptibility to errors due to known limits on human capabilities, such as rapid wearing out when performing routinely repetitive tasks, cognitive biases, and the like. One technical problem dealt with by the present disclosure is to overcome such drawbacks and disadvantages of manual screening.

A device for automated health check of passengers of a vehicle in accordance with the disclosed subject matter may be deployed at locations and venues where a plurality of individuals may arrive at or pass through by vehicle, such as for example at entrance gates to parking lots, checkpoints in border passages or toll highways, temporary roadblocks erected by police patrols, and the like. In some exemplary embodiments the device may be physically designed as a kiosk, similarly to vending machines or ticket dispensers used for example in automatic supply and charging of payment for services or products and the like. Optionally the device may be operating in coordination with at least one physical or logical transport regulating device or arrangement, such as for example a barrier gate, a set of one or more retractable bollards, a traffic light, and/or the like. The transport regulating device may be configured to grant permission or allow passage therethrough only in condition that all passengers of the vehicle are cleared by the automated health check device as disclosed herein.

The device may comprise vital signs sensor(s), imaging sensor(s) and processor(s). The vital signs sensor(s) may be configured for measuring health parameter(s) of a passenger of a vehicle, such as a body temperature, a breathing rate, a breathing depth (i.e., a tidal respiratory volume over time), a heart rate, a heart rate stability, cough presence, a blood oxygenation level, a voice-indicated nasal congestion and/or throat irritation, and/or the like. The vital signs sensor(s) may be mounted on the device at a height of between about 1.2 meters and about 1.6 meters to provide a field of view covering at least a portion of an area confined by a side window of a vehicle. Optionally a plurality of copies of the vital signs sensor(s) may be mounted on the device at different heights to accommodate for various vehicle heights, such as for example a car, a truck, a sports utility vehicle (SUV), and/or the like. The vital signs sensor(s) and/or the imaging sensor(s) may comprise a video camera, a thermal camera, a depth camera, an ultra-wideband radar, a laser speckle imaging device, a microphone, an ultrasonic sensor, a radiance sensor, a laser Doppler vibrometer, and/or the like. Optionally the imaging sensor(s) and vital signs sensor(s) may be one and a same type of sensor(s) or integrated into a single sensor such as, for example, a thermal camera configured for obtaining thermography of the vehicle cabin area depicting measurement(s) of body temperature of each of the passengers of the vehicle. The vital signs sensor(s) may be sanitized and/or sterilized between successive uses as required to avoid contamination thereof, for example using ultraviolet (UV) radiation, chemical disinfectant, and/or the like.

The processor(s) may be configured for acquiring image(s) from the imaging sensor(s) of at least an area confined by a window of the vehicle where a passenger may be present at. The processor(s) may analyze the image(s) to determine location of the window and of the passenger and accordingly determine whether the vital signs sensor(s) being oriented to a predetermined point of view in relation to the passenger. The processor(s) may then employ the vital signs sensor(s) to obtain measurement(s) of health parameter(s) of the passenger. Optionally the processor(s) may acquire and process data gathered by either the imaging sensor(s), the vital signs sensor(s), or both to determine personal parameter(s) of the passenger such as an age, a gender, a weight, a height, an ethnicity and/or race, and likewise physical or biological characteristics. Optionally image data gathered by the imaging sensor(s) may be analyzed by the processor(s) using face recognition technique(s) or the like.

Optionally prior to obtaining the measurement(s) the vital signs sensor(s) may be reoriented to the predetermined point of view relative to the passenger as needed, for example due to expected difficulty of some drivers to accurately position the vehicle at a designated spot, variance in response time and adherence to directions of different drivers or even a same driver under different circumstances, variance in dimensions of different vehicles and possible motion constraints imposed thereby (e.g. in case the device being deployed adjacent to a gate barrier forcing vehicles to stop in front thereof, vehicles of different lengths may be stopped at different angular distances from the device), and/or the like. Reorientation of the vital signs sensor(s) may be performed using a mechanical assembly on which the vital signs sensor(s) may be mounted, such as an arrangement of one or more gimbals or the like. The mechanical assembly may be an untethered one, such as for example a lightweight unmanned aircraft vehicle (UAV), i.e. a commercially available drone or the like. Additionally or alternatively, reorientation of the vital signs sensor(s) may be performed electronically, such as for example in case the vital signs sensor(s) comprise at least one electronically steerable radar or the like. Optionally a plurality of vital signs sensors in array or grid arrangement may be deployed so as to provide an omnidirectional or multiple angles coverage of a plurality of areas confined by different windows of the vehicle when arriving at a designated stopping point or perimeter. For example, one or more rows of vital signs sensor(s) optionally consisting several copies each may be disposed along opposite sides laterally to the travelling direction of incoming vehicles such that an aggregated field-of-view of the plurality of vital signs sensor(s) may achieve coverage of all four side windows of a commercially available private car when standing in pose therebetween.

Optionally the device in accordance with the disclosed subject matter may comprise a user interface configured for communicating instructions to passenger(s) and/or an operator of the vehicle, the operator being either a human driver or a computerized apparatus, such as for example in case of an autonomous vehicle operated by a computing device executing code instructions. The user interface may comprise a display panel or screen for projecting visually perceived stimuli such as graphics, lights, printed text and/or the like. Additionally or alternatively, the user interface may comprise a speaker for providing aurally perceived stimuli such as sounds, tones, speech, voiced text and/or the like. In some exemplary embodiments, reorientation of the vital signs sensor(s) may be notionally achieved by providing, via the user interface, instructions to the operator of the vehicle to direct the vehicle to a determined location, thereby placing the passenger at a position and orientation in alignment with the predetermined point of view of the vital signs sensor(s) relative to the passenger.

Optionally the imaging sensor(s) may comprise spatial sensor(s) for capturing depth data, such as a time-of-light (ToF) camera, a three-dimensional scanner e.g. using laser or structured light projections, and likewise depth mapping techniques and/or combinations thereof, as employed for example in commercially available motion sensing input devices such as Kinect by Microsoft. The spatial sensor(s) may obtain depth data of at least an area confined by a window of the vehicle, preferably where a passenger of the vehicle may be present at or been previously detected e.g. based on analysis by the processor(s) of imaging data acquired from the imaging sensor(s). The processor(s) may analyze the depth data from the spatial sensor(s) to determine whether the respective window being in a rolled down position allowing clear line-of-sight between the vital signs sensor(s) and the passenger. Optionally prior to obtaining the measurement the user interface may be used by the processor(s) to provide instructions to a passenger or an operator of the vehicle to roll and maintain the window down for duration of the measurement, in case of a finding that the window being closed or only partially open such that it obstructs visibility or reachability of the passenger by the vital signs sensor(s).

Optionally the imaging sensor(s) may comprise thermal sensor(s) for acquiring temperature data, such as an Infra- Red (IR) sensor, a Resistance Temperature Detector (RTD), a thermocouple (TC) sensor, a thermistor temperature sensor, a thermometer, a semiconductor Integrated Circuit (IC) temperature sensor, or the like. The processor(s) may obtain and analyze temperature data acquired by the thermal sensor(s) to determine thermal conditions at an area of the vehicle where a passenger may be present, such as by a window and/or somewhere else in the cabin.

Optionally the processor(s) may determine a calibration required to the vital sensor(s) prior to obtaining measurement(s) therefrom in order to mitigate or cancel out an adverse influence on the measurement(s) due to the thermal conditions within the vehicle. Such calibration may be determined based on contextual factors such as relative differences between thermal conditions inside and outside of the vehicle, for example, and/or absolute factors such as lower and upper bounds on ambient temperature value, a signal-to-noise ratio, or the like.

Additionally or alternatively the temperature data may be analyzed by the processor(s) to determine whether a climate control system of the vehicle, such as a vehicle heating, ventilation, and air conditioning (HVAC) system or the like is being operated. The analysis may be performed for example using pattern recognition techniques to detect patterns in the temperature data indicative of climate control system usage. The processor(s) may provide via the user interface instructions to an operator of the vehicle to turn and maintain off the climate control system for duration of the measurement, in order to ensure proper functioning of the vital signs sensor(s).

Additionally or alternatively in order of mitigating or overcoming the thermal conditions in the vehicle the processor(s) may provide via the user interface instructions to passenger(s) of the vehicle to extend a predetermined body portion out of the window, e.g. a palm, an arm, a head, or the like, and/or to make accessible a predetermined inner cavity portion at a body orifice, e.g. a mouth opening, a nostril, an ear canal, or the like.

The processor(s) may acquire from the imaging sensor(s) image data of the vehicle and process it in real-time to determine at least one of a location, a velocity, and/or an acceleration or deceleration of the vehicle, i.e. motion tracking. Optionally the imaging sensor(s) may comprise at least one imaging sensor such as a camera or the like being located at an altitude above ground of between about 2.5 meters and about 5 meters and being directed downwards to provide a top view of at least a portion of the vehicle and at least one reference location marker to allow the processor(s) to determine based on the image data whether the vehicle stopped at desired position or what corrective translation may be needed otherwise. The user interface may be employed for providing instructions to the operator of the vehicle to slow down and/or to stop the vehicle at a designated location and/or pose. The instructions may be generated on-demand in accordance with the motion tracking calculations performed by the processor(s) using the image data. In some exemplary embodiments, once the vehicle reaches a full stop the processor(s) may determine whether the vital signs sensor(s) are at a measurement obtainment range from a passenger, for example by determining whether the vital signs sensor(s) being at a distance from a location of a relevant marker, e.g. a window at an area where the passenger may be located, which equals or falls under a predetermined threshold. The threshold may be either statically assigned, based on known industry range limits of the vital signs sensor(s) for example, or dynamically determined by taking into account variable field parameters, such as local weather conditions or the like. In case of a determination that the distance exceeds the threshold the processor(s) may calculate a corrective translation of the vehicle and provide via the user interface instructions to an operator of the vehicle for effecting the same and bringing the vehicle into a desired spot.

Additionally or alternatively, the image data acquired from the imaging sensor(s) may be analyzed by the processor(s) to determine an extent of shakes or vibrations of the vehicle. Optionally the analysis of the image data may further comprise a determination of a frequency of the vibrations. The frequency may be removed from respective measurements obtained from the vital signs sensor(s). For example, while being in idle mode i.e. in full stop yet with engine still running, the vehicle may exhibit vibrations at frequencies of 3 Hz or lower, which may be of significance in the context of heart rate measurement thus skewing the health check results. In some exemplary embodiments the operator of the vehicle may be instructed via the user interface to turn and maintain the engine off for the duration of the measurement. Optionally such course of action for mitigating and/or overcoming disruptions to measurement(s) obtainment due to vibrations or shaking may be employed selectively e.g. only in cases where a frequency of the vibrations exceeds a predetermined threshold.

Optionally the image data acquired from the imaging sensor(s) may be analyzed by the processor(s) to determine for each of the passengers in the vehicle a distinct location of the respective passenger along a longitudinal axis of the vehicle. For example, in a car with left and right front seats and an integrated backseat there may be any number of passengers between one and five and up to two or three distinct locations of passengers occupying the vehicle, for example a first passenger may be a driver occupying the seat at the wheel, e.g. the left front seat, a second passenger may occupy the right front seat which may be either aligned with the left seat or indented forward or backward relative thereto, a third passenger may occupy one of three available spots in the backseat, and so forth. The processor(s) may calculate a plan for conducting the health check to the group of passengers at the vehicle in entirety, taking into account a configuration of the vital signs sensor(s), e.g. number and deployment thereof. The plan may entail a total number and whereabouts of halting points for the vehicle to reach at and stand therein for allowing satisfactory conditions for the measurement(s) to take place. For example, in case there are two vital sensors overall being located at each side of the vehicle, and there are four passengers in the vehicle, two of which in the front seats substantially at a same point along the longitudinal axis of the vehicle and two in the backseat, then the processor(s) may determine first and second halting points in which the two vital signs sensors may be oriented to a predetermined point of view relative to the front-seated and back-seated passengers respectively.

Optionally the image data acquired from the imaging sensor(s) may be analyzed by the processor(s) to extract therefrom a unique identifier of the vehicle, such as for example a license plate number. Optionally additional attribute(s) of the vehicle may be detected, such as category, color, manufacturer, model, and the like. The identification data of the vehicle comprised of the unique identifier and optionally the additional attribute(s) may be recorded by the processor(s) along with the measurement(s) obtained from the vital signs sensor(s) for each of the passengers of the vehicle. The processor(s) may be configured to provide an output associating the identification data and measurement(s) integrally. The output may be communicated to other gateways for alerting and preventing passage of the vehicle therethrough in case of suspect or abnormal results found in the measurement(s) and/or to a processing center for further analysis and consultation.

In some exemplary embodiments, the device and/or methods in accordance with the disclosed subject matter may be used as security measures, for example, in detection of fraudulent identity representation in the context of access control systems. Optionally measurement(s) obtained from the vital signs sensor(s) may be used to determine whether a passenger being inspected is indeed presenting herself to the imaging sensor(s) and not a fraudulent depiction, such as by use of a photograph, a mask, a computer screen, and/or the like.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is noted that the term "window" as used herein may refer to an aperture laterally bordering a vehicle cabin that may be adapted for selectively and interchangeably being opened or closed, fully or partially.

Reference is now made to FIG. 1, which is a block diagram of a device for automated health check of passengers of a vehicle, in accordance with some embodiments of the present invention. One or more acts of the methods described with reference to FIGS. 2-6 may be implemented by device 100 and/or components thereof, as described herein, for example, by processor(s) 103 of a device 100 executing code instructions stored in a memory (also referred to as a program store) 104.

Device 100 may include and/or be in communication with one or more imaging sensor(s) 101, configured for acquiring at least one image of at least an area confined by a window of a vehicle where a passenger may be located at. Imaging sensor(s) 101 may comprise a video or digital camera, such as a charged-couple device (CCD) camera, a Complementary metal-oxide-semiconductor (CMOS) camera, or a likewise photosensitive device configured for capturing and producing images in grayscale, Red-Green-Blue (RGB) color, raw and/or other industry accepted image format(s). Optionally imaging sensor(s) 101 may comprise a spatial sensor such as a time-of-light (ToF) camera, a three-dimensional scanner, an ultra-wideband (UWB) radar, or any likewise range mapping device, adapted for acquiring depth data of at least the area confined by the window. Additionally or alternatively, imaging sensor(s) 101 may comprise an acoustic sensor adapted for sound-based surface mapping, such as a surface acoustic wave (SAW) sensor or the like. In some exemplary embodiments imaging sensor(s) 101 may comprise a thermal sensor such as an infrared camera adapted for acquiring temperature data of at least the area confined by the window.

Device 100 may include and/or be in communication with one or more vital signs sensor(s) 102, configured for measuring health parameter(s) of passenger(s) of a vehicle, such as for example a body temperature, a breathing rate, a breathing depth, a heart rate, a heart rate stability, a blood oxygenation level, and/or the like. Alternatively or additionally, vital sign sensor(s) 102 may be adapted for collecting a voice sample from each passenger of the vehicle to allow detection of illness symptoms that might be indicated therein, such as a nasal congestion, a throat irritation, and/or the like, for example by using soundwave frequency analysis. Similarly, vital sign sensor(s) 102 may be further or otherwise adapted to collect an audio and/or video sample of each passenger wherein symptoms such as for example cough presence or the like may be detected. Processing and/or analysis of vital signs data such as measurement(s) and/or sample(s) gathered by vital signs sensor(s) 102 may be performed by processor(s) 103 as described herein and/or by an external device being in communication with Device 100.

Device 100 may gather imaging data sensed by imaging sensors 101 and/or vital signs data sensed by vital signs sensor(s) 102, via one or more data buses or interfaces, for example, a network interface, a wire connection, a wireless connection, a local bus, other physical interface implementations, and/or virtual interfaces (e.g., software interface, application programming interface (API), software development kit (SDK)).

Device 100 may be implemented as, for example, a standalone unit, a client terminal, a server, a computing cloud, a mobile device, a desktop computer, a thin client, a Smartphone, a Tablet computer, a laptop computer, a wearable computer, glasses computer, and a watch computer. Device 100 may be implemented as a customized unit that include locally stored software and/or hardware that perform one or more of the acts described with reference to FIGS. 2-5. Alternatively or additionally, Device 100 may be implemented as code instructions loaded on an existing computing device. Alternatively or additionally, Device 100 may be implemented as hardware and/or code instructions (e.g., an accelerator card) installed and/or integrated within an existing computing device.

Processor(s) 103 of device 100 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 103 may include one or more processors (homogenous or heterogeneous), which may be arranged for parallel processing, as clusters and/or as one or more multi core processing units.

Memory (also known herein as a data storage device) 104 stores code instructions executable by processor(s) 103, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 104 stores code instruction that implement one or more acts of the methods described with reference to FIGS. 2-5. Alternatively or additionally, one or more acts of the methods described with reference to FIGS. 2-5 are implemented in hardware.

Device 100 may include a data storage device for storing data, for example, a database that stores records of specifications of each sensor type(s) of imaging sensor(s) 101 and vital signs sensor(s) 102 used by device 100 and optionally their respective settings. Data storage device of device 100 may be implemented as, for example, a memory, a local hard-drive, a removable storage unit, an optical disk, a storage device, and/or as a remote server and/or computing cloud (e.g., accessed via a network connection).

Device 100 includes and/or is in communication with a user interface 105 that includes a mechanism for a user to enter data or other input (e.g., vehicle information, passenger information, etc.) and/or view, listen to or otherwise perceive presented data or output (e.g., instructions or guidance regarding a preferred spot for the vehicle to stop and stand at for the measurement(s), instructions to passengers to roll down windows and/or to extend body portions outside thereof, and so forth). Exemplary user interfaces 105 include, for example, one or more of, a touchscreen, a display, a keyboard, a mouse, and voice activated software using speaker(s) and microphone(s). External devices communicating with device 100 may serve as user interfaces 105, for example, a smartphone running an application may establish communication (e.g., cellular, network, short range wireless) with device 100 using a communication interface (e.g., network interface, cellular interface, short range wireless network interface). The user may enter data and/or view data on the display of the smartphone, optionally via a graphical user interface (GUI) application, listen to or enter audio data via speaker(s) and microphone(s), and/or receive output from or provide input to device 100 using likewise input/output interface(s) available by the smartphone, as for example tactile feedback through vibrations.

Figure 2:
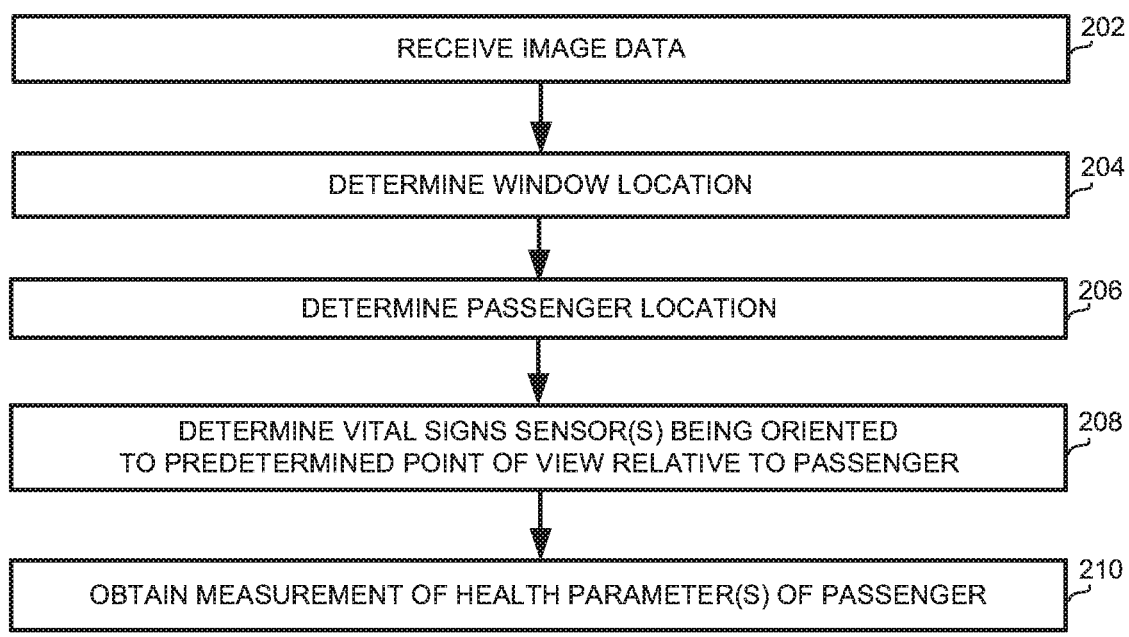
FIGS. 2, 3, 4, 5 and 6 are flowcharts of methods of operation of a device for automated health check of passengers of a vehicle, in accordance with some embodiments of the present invention.

Reference is now made to FIG. 2 which is a flowchart of a method of operation of a device for automated health check of passengers of a vehicle, in accordance with some embodiments of the present invention.

At 202 image data may be received, optionally from imaging sensor(s) such as 101 in FIG. 1. The image data may comprise one or more images, a video stream, and/or the like, preferably capturing at least an area confined by a window of the vehicle. Optionally the image data may be acquired from a plurality of sources or source types, so as to provide multidirectional, multispectral, and/or likewise multi-layered image data, for example, the imaging sensor(s) from which image data may be obtained may comprise an arrangement of several digital video cameras positioned at different viewpoints, an array of at least one digital video camera and at least one infrared camera with respective fields of view (FOVs) at least partially overlapping, and/or the like.

At 204 location of the window captured in the image data may be determined, for example using digital image processing and computer vision techniques. Optionally locating the window in an image may be performed based on the regularity of shape of windows in vehicles and/or of the vehicles as well. Optionally location of the window in the image may be readily mapped into real world coordinates, for example using known camera parameters such as point of view and focal length.

At 206 location of a passenger of the vehicle may be determined, optionally based on the location of the window as determined at 204. Optionally determination of the whereabouts of the passenger may be performed based on standard measures and proportions of windows and seats adjacent thereto in vehicles. For example, given the location of the window, the passenger may be presumed as located at about a foot distance from the window towards the central longitudinal axis of the vehicle. Optionally the passenger's location may be estimated at further precision using face recognition or likewise technique.

At 208 determination may be made as to whether vital signs sensor(s) such as 102 of FIG. 1, deployed in a perimeter of the vehicle, are oriented to a predetermined point of view relative to the passenger, optionally based on the passenger's location determined on Step 206. Optionally the determination may be made based on known field of view (FOV) parameter of vital signs sensor(s) and an intersection thereof with the location determined for the passenger.

At 210 at least one measurement of at least one health parameter of the passenger may be obtained from vital signs sensor(s). Optionally if multiple health parameters measurement being required, a portion of health parameters may be measured simultaneously, for example, a heart rate and a body temperature may be measured each by stand-alone sensor operating concurrently at a same time, whereas a remainder of health parameters may be measured sequentially, for example, a heart rate and/or a breathing rate may be measured at time apart of when voice-indicated symptom(s) being measured. Optionally data sensed by vital signs sensor(s) during a same measurement may be used to determine different health parameters, for example, heart rate and blood oxygen saturation may be both measured by amount of shined light scattering off blood vessels, as in some optical vital signs sensors commercially available.

Figure 3:
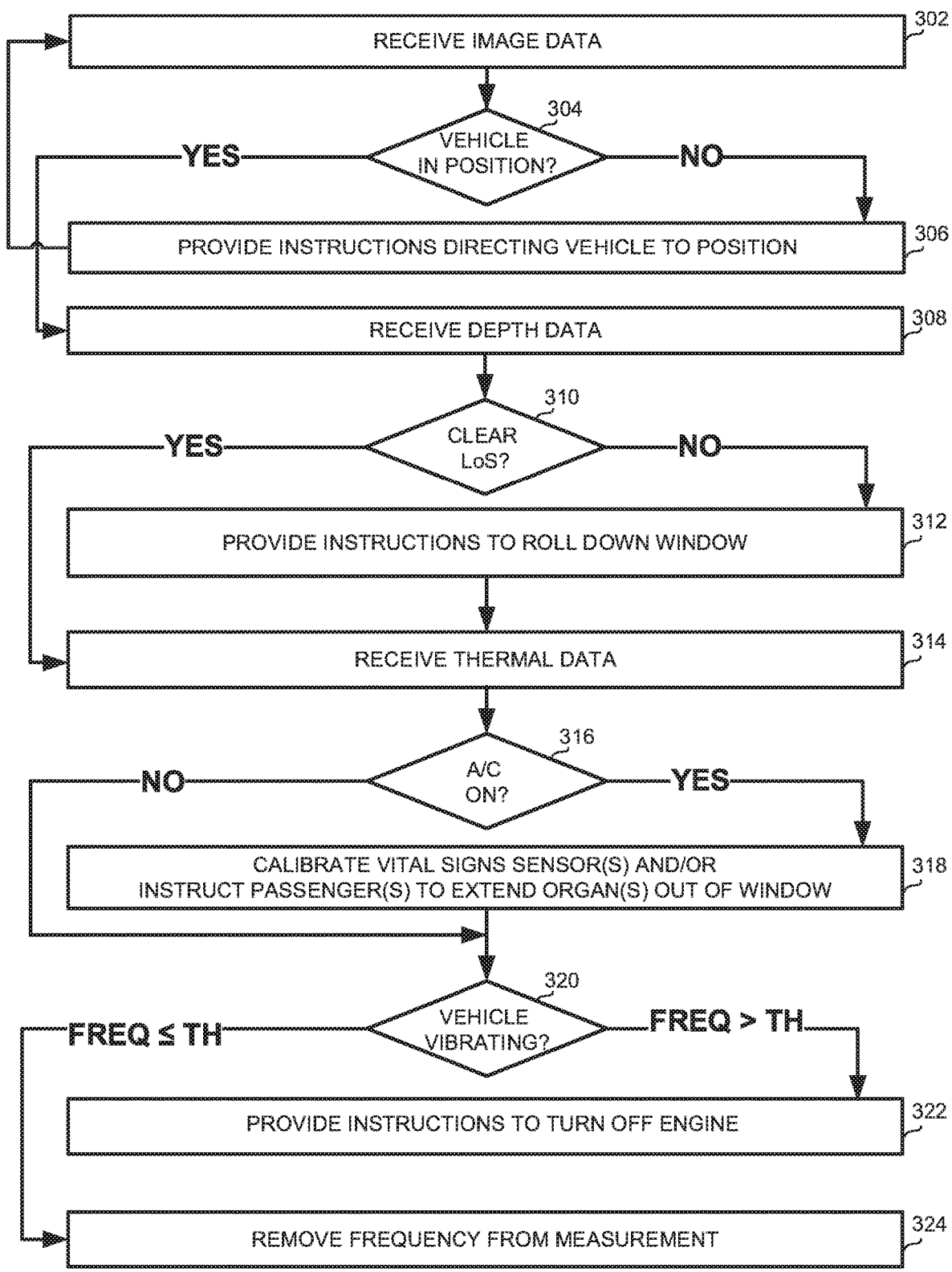

Reference is now made to FIG. 3 which is a flowchart of another method of operation of a device for automated health check of passengers of a vehicle, in accordance with some embodiments of the present invention.

At 302 image data may be received, similarly as in 202 of FIG. 2. At 304 determination whether the vehicle being in position enabling measurement by vital signs sensor(s) be performed. Optionally the determination may be made using image data received at 302, for example, a diameter of the vehicle may be detected in an image and a bounding box, sphere or the like enclosing the vehicle diameter may be computed and correlated with a boundary of a designated perimeter. At 306 if the vehicle was found at 304 out of position, instructions for directing the vehicle into position may be provided, for example via user interface such as 105 of FIG. 1. Optionally the procedure from 302 to 306 may be reiterated as needed until the vehicle has been placed in satisfactory position, in which case the procedure may move forward to 308.

At 308 depth data may be received, optionally from a spatial sensor being comprised in imaging sensor(s) such as 101 of FIG. 1. Preferably the depth data may capture at least an area of a window of the vehicle where a passenger may be located at. At 310 determination may be made as to whether a clear line of sight (LoS) exists between the passenger and vital signs sensor(s) such as 102 of FIG. 1. Optionally the determination regarding a clear LoS existence may be made using the depth data received at 308. Alternatively or additionally, existence or lack of LoS may be established based on known physical properties of certain materials, for example, glass objects may be transparent to light and opaque to heat, thus an opaque surface featured in thermal imaging of the vehicle, such as may be received at 314 as described herein, may be indicative of closed window obstructing LoS to the passenger. At 312 responsive to lack of clear LoS being determined at 310, instructions may be provided to roll down window to allow completion of the automated health check procedure. Otherwise the procedure may skip ahead to 314.

At 314 thermal data may be received, optionally from a thermal sensor comprised among imaging sensor(s) such as 101 of FIG. 1. Preferably the thermal data may capture at least temperature data within a cabin area of the vehicle. Optionally the thermal data may comprise thermography of the vehicle cabin. At 316 determination may be made as to whether a climate control system of the vehicle, such as an air conditioner (A/C) or the like, being in operation and/or recently operated, for example by applying pattern recognition analysis on thermal data received at 314 to detect patterns therein conforming to climate control system usage. At 318 responsive to determination made at 316 that the climate control system being on, a mitigating calibration of vital signs sensor(s) may be calculated and implemented, and/or instructions to passenger(s) of the vehicle to extend organ(s) out of window, in mitigation of thermal conditions of the vehicle, may be provided where appropriate. Optionally compliance to instructions by passenger(s) may be verified, for example, by applying gesture recognition analysis or likewise technique to image data which may be received as in 302.

At 318 determination may be made as to whether the vehicle is vibrating, for example by motion detection or likewise image processing analysis of image data at 302. Alternatively or additionally a specialized sensor may be used, for example, a laser Doppler vibrometer (LDV) or the like. Optionally a frequency of the vibrations may be determined and compared to a predetermined threshold for assessment of possible affect thereof on measurement performed by vital signs sensor(s). At 322 responsive to the frequency exceeding the predetermined threshold, instructions to turn off engine of the vehicle may be provided. Otherwise at 324 the frequency may optionally be removed from the measurement where applicable.

Figure 4:
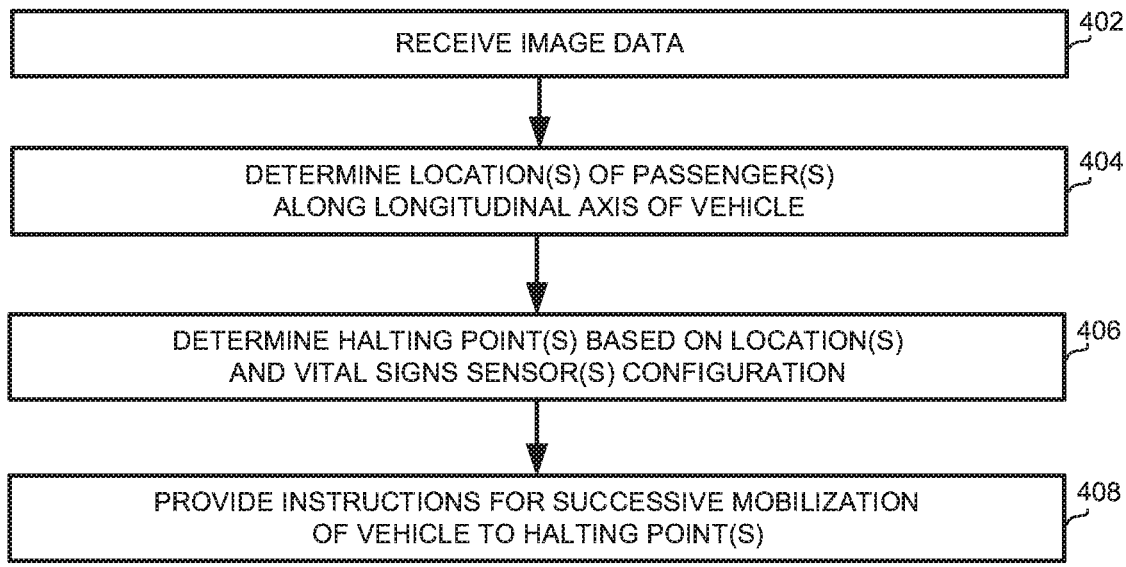

Reference is now made to FIG. 4 which is a flowchart of yet another method of operation of a device for automated health check of passengers of a vehicle, in accordance with some embodiments of the present invention.

At 402 image data may be received, similarly as in 202 of FIG. 2 or as in 302 of FIG. 3. At 404 one or more distinct locations of passengers along a longitudinal axis of the vehicle may be determined. Optionally passengers of the vehicle may be identified in image data received at 402, for example using face recognition analysis, and location of each passenger within the vehicle may be initially determined. The initial determination of location of each passenger may then be projected onto the longitudinal axis of the vehicle. Optionally projected locations at disparity below a predetermined threshold may be merged together into a single distinct location. At 406 one or more halting points may be determined based on the distinct location(s) determined at 404 and configuration of vital signs sensor(s) deployed on premise, such as described herein with reference to FIGS. 7A-7C. At 408 instructions may provide to successively mobilize the vehicle to the halting point(s) determined at 406.

Figure 5:
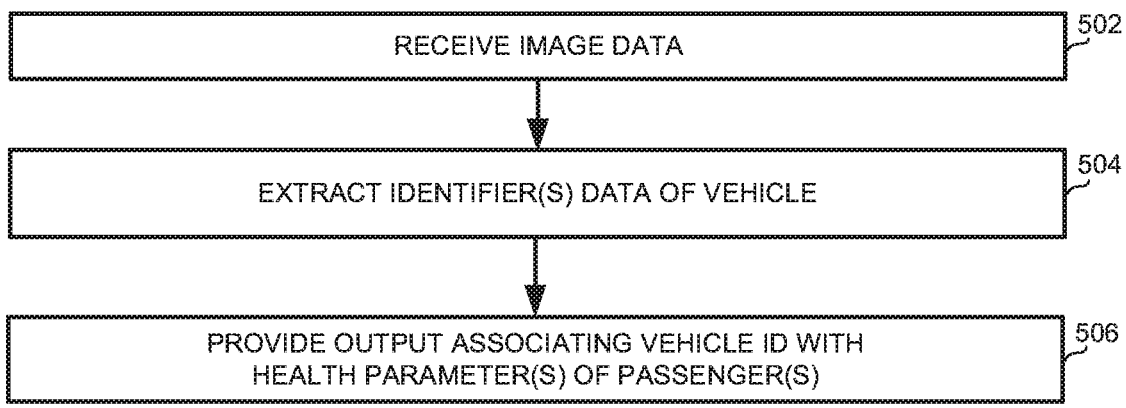

Reference is now made to FIG. 5 which is a flowchart of yet another method of operation of a device for automated health check of passengers of a vehicle, in accordance with some embodiments of the present invention.

At 502 image data may be received, similarly as in 202, 302 and/or 402 of FIGS. 2-4 respectively. At 504 one or more identifiers of the vehicle may be extracted, optionally using image data received at 502. Optionally identifiers of the vehicle may include at least one unique identifier, such as a license plate number, a chassis number (where available), or the like. Other identifiers may additionally or alternatively be extracted, such as a category (e.g. size-based and/or body style type), a color, a model and/or manufacturer, and the like. At 506 an output associating the vehicle's identifying data, as extracted at 504, with health parameter(s) of the vehicle's passenger(s), optionally obtained by acts and methods as described herein with reference to FIGS. 2-4, may be provided.

Figure 6:
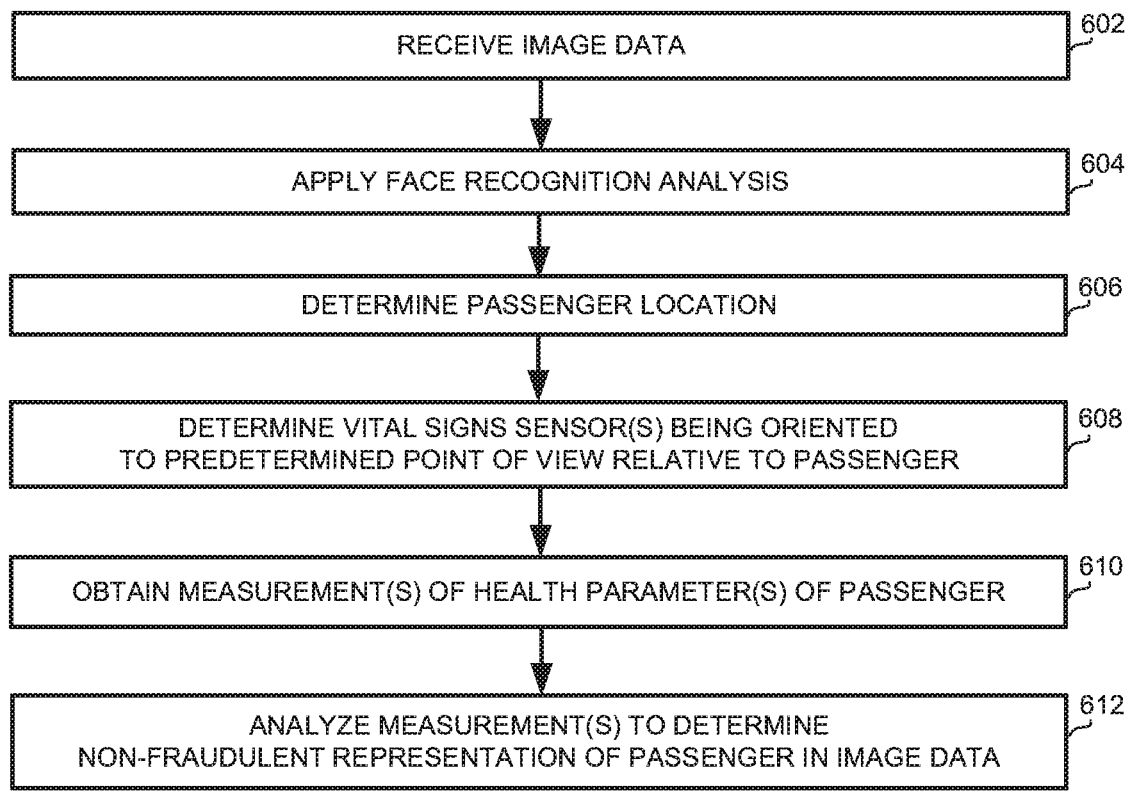

Reference is now made to FIG. 6 which is a flowchart of yet another method of operation of a device for automated health check of passengers of a vehicle, in accordance with some embodiments of the present invention.

At 602 image data may be received, similarly as in 202, 302, 402 and/or 502 of FIGS. 2-5 respectively. At 604 face recognition analysis may be applied to the image data received at 602 to detect appeared presence of a passenger in the vehicle. At 606 location of the passenger detected at 604 may be determined, optionally based on an output of the face recognition analysis performed at 604 and/or by further analysis of the image data received at 602. At 608 determination as to whether vital signs sensor(s) being oriented to predetermined point of view relative to the passenger may be made, similarly as at 208 of FIG. 2. At 610 measurement(s) of health parameter(s) of the passenger may be obtained from the vital signs sensor(s), similarly as at 210 of FIG. 2. At 612 measurement(s) obtained at 610 may be analyzed to determine whether representation of the passenger in the image data received at 602 being non-fraudulent.

Figure 7A:
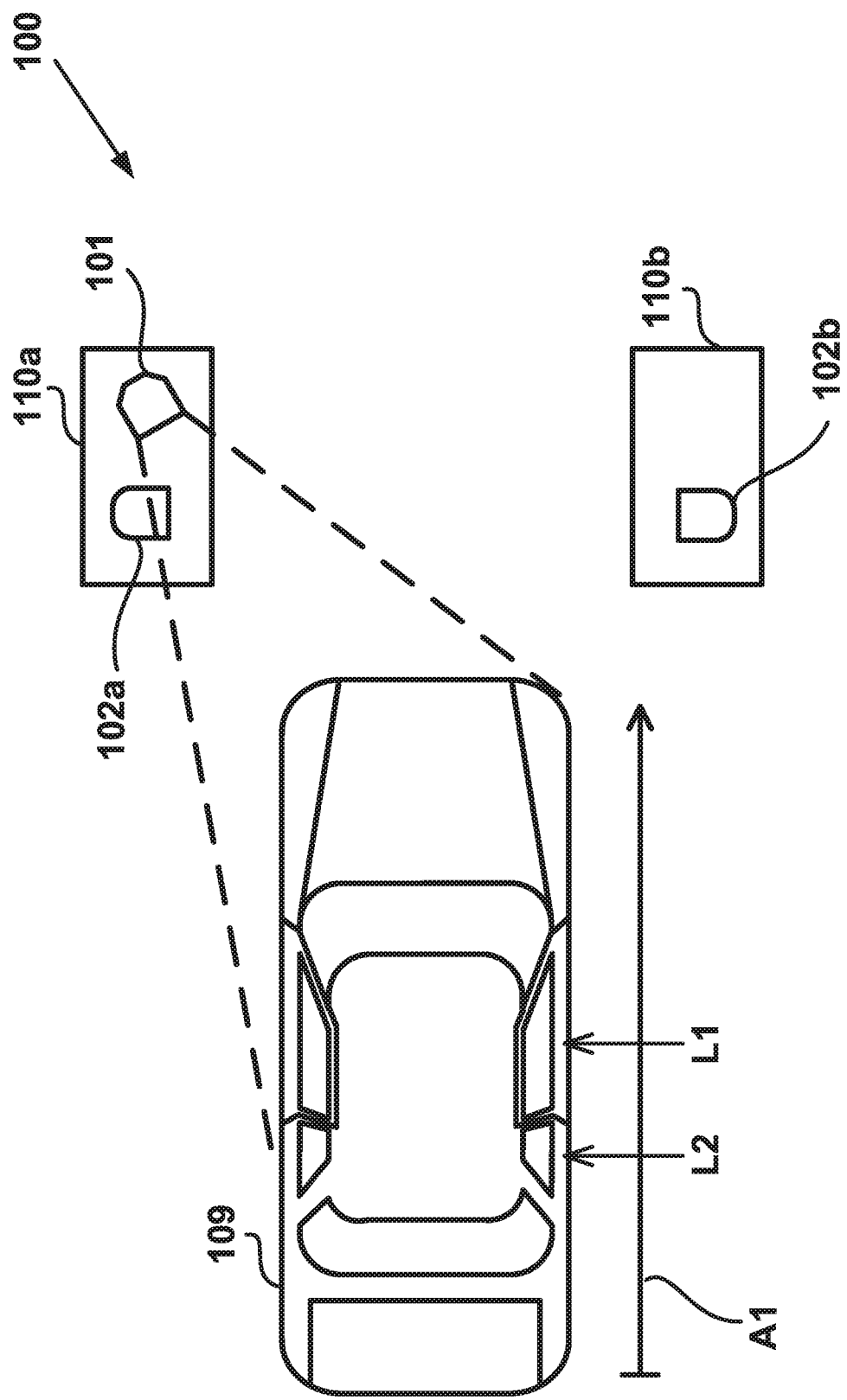
FIGS. 7A, 7B and 7C are schematic illustrations of exemplary device and method for automated health check of passengers of a vehicle, in accordance with some embodiments of the present invention.
Figure 7B:
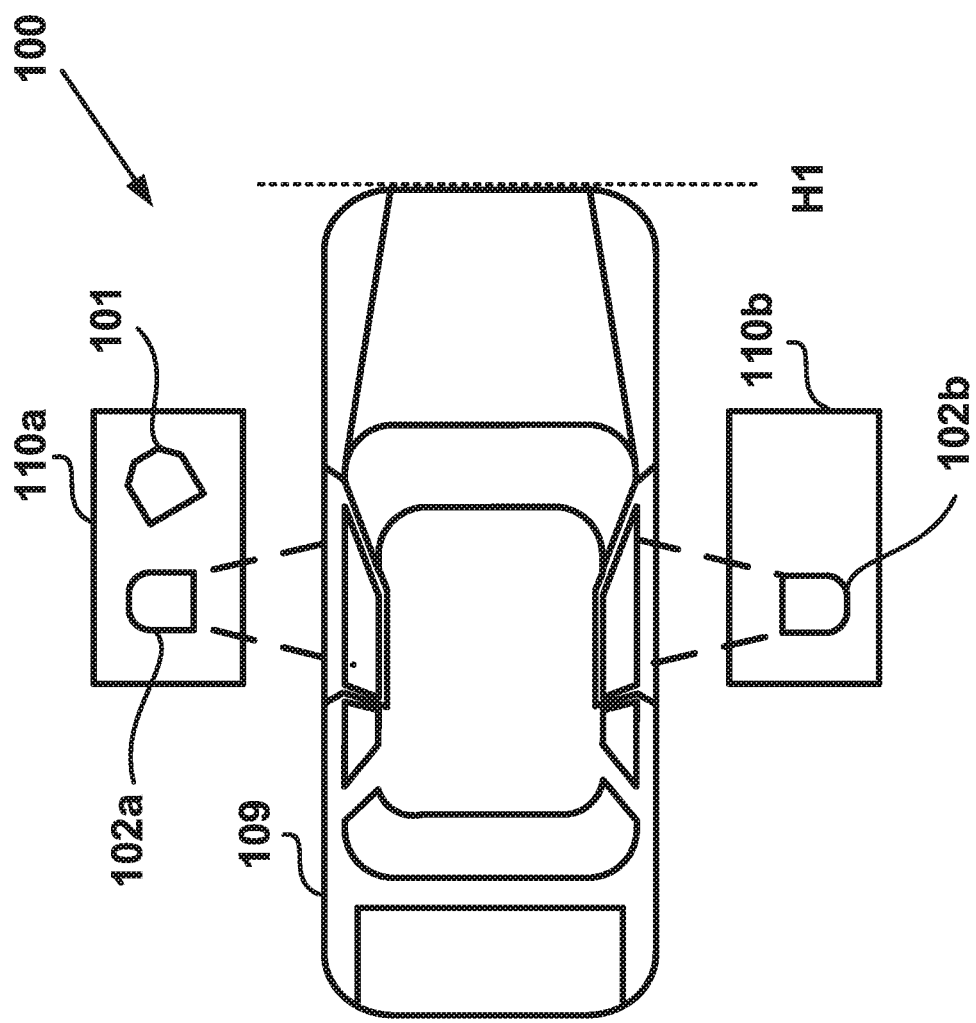
Figure 7C:
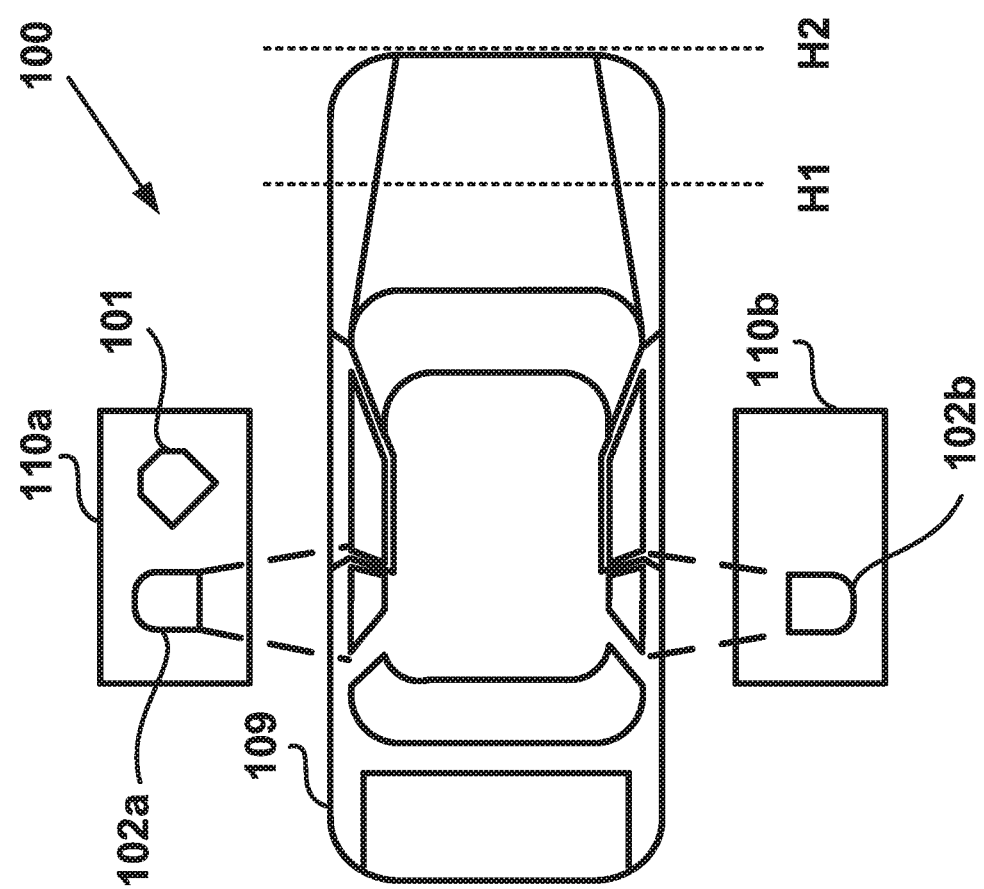

Reference is now made to FIGS. 7A-7C which are schematic illustrations of exemplary device and method for automated health check of passengers of a vehicle, in accordance with some embodiments of the present invention.

Device 100 such as described herein with reference to FIG. 1 may be deployed over a first and second kiosks 110a and 110b. Device 100 may comprise one or more imaging sensor(s) 101 and at least a first and second vital signs sensors 102a and 102b. Without loss of generality, imaging sensor(s) 101 and vital signs sensor 102a may be mounted on kiosk 110a, and vital signs sensor 102b may be mounted on kiosk 110b.

As shown in FIG. 7A, device 100 may acquire via imaging sensor(s) 101 image data of a vehicle 109. The image data may be analyzed (e.g. by processor(s) 103 executing code instructions stored in memory 104 as described herein with reference to FIG. 1) to determine at least one halting point for vehicle 109 based on distinct location(s) of passengers thereof and configuration of vital signs sensors 102a and 102b, similarly as described herein with reference to FIG. 4. Instructions for halting the vehicle at the at least one halting point may be provided by device 100 for example via user interface 105 as described herein with reference to FIG. 1.

As shown in FIG. 7B, a first halting point H1 for vehicle 109 may be determined such that vital signs sensor 102a may be in alignment with front left-side window of vehicle 109 and vital signs sensor 102b may be in alignment with front right-side window of vehicle 109. Halting point H1 may correspond to scenarios wherein a driver or a driver and a passenger in the seat next to the driver are riding vehicle 109, for example. Optionally image data of vehicle 109 may be acquired via imaging sensor(s) 101 continuously or periodically and analyzed by processor(s) of device 100 to validate that vehicle 109 stopped at halting point H1 as instructed.

As shown in FIG. 7C, a second halting point H2 for vehicle 109 in addition to the first halting point H2 may be determined such that vital signs sensor 102a may be in alignment with back left-side window of vehicle 109 and vital signs sensor 102b may be in alignment with back right-side window of vehicle 109. Halting point H2 may correspond to scenarios wherein at least one passenger in the backseat is riding vehicle 109, for example. Optionally image data of vehicle 109 from imaging sensor(s) 101 may be acquired and analyzed to validate that vehicle 109 moved out of halting point H1 onwards into halting point H2 and stopped there as instructed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant devices and methods for automated health check of vehicle passengers will be developed and the scope of the term automated health check of vehicle passengers is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for automated health check of passengers of a vehicle, comprising:
    at least one imaging sensor configured for capturing at least one image of at least an area confined by a window of the vehicle;
    at least one vital signs sensor configured for measuring a health parameter of a passenger at the area confined by the window;
    at least one processor configured for:
        acquiring and analyzing said at least one image to determine location of the window;
        determining based on the determined location of the window a location of the passenger;
        determining said at least one vital signs sensor being oriented to a predetermined point of view in relation to the location of the passenger determined; and
        obtaining a measurement of the health parameter of the passenger from said at least one vital signs sensor.

2. The device of claim 1, further comprising at least one mechanical assembly configured for reorienting the at least one vital signs sensor, wherein said at least one processor being further configured for instructing the at least one mechanical assembly to reorient said at least one vital signs sensor to the predetermined point of view.

3. The device of claim 1, wherein said at least one vital signs sensor comprising an electronically steerable radar, wherein said at least one processor being further configured for reorienting said electronically steerable radar to the predetermined point of view.

4. The device of claim 1, further comprising a user interface for providing output, wherein said at least one processor being further configured for providing via the user interface instructions to the passenger to move at least a body portion for placing said at least one vital signs sensor in orientation to the predetermined point of view.

5. The device of claim 1, wherein said at least one imaging sensor comprising at least one spatial sensor configured for obtaining depth data of at least the area confined by the window, wherein said at least one processor being further configured for analyzing said depth data to determine whether the window being in a rolled down position allowing clear line-of-sight between said at least one vital signs sensor and the passenger.

6. The device of claim 5, further comprising a user interface for providing output, wherein said at least one processor being further configured for: prior to said obtaining the measurement and responsive to determination that the window being in position not allowing clear line-of-sight between said at least one vital signs sensor and the passenger, providing via the user interface instructions to an operator of the vehicle to roll and maintain the window down for duration of the measurement.

7. The device of claim 1, further comprising a user interface for providing output, wherein said at least one processor being further configured for:
    prior to said obtaining the measurement and responsive to determination that the location of the window exceeding a predetermined threshold distance in relation to said at least one vital signs sensor, determining a corrective translation of the vehicle relocating the window within the predetermined threshold distance, and
    providing via the user interface instructions to an operator of the vehicle for effecting the corrective translation.

8. The device of claim 1, wherein said at least one imaging sensor comprising at least one thermal sensor configured for obtaining temperature data of at least the area confined by the window, wherein said at least one processor being further configured for analyzing said temperature data to determine whether thermal conditions in the vehicle enable proper functioning of said at least one vital signs sensor.

9. The device of claim 8, wherein said at least one processor being further configured for determining and effecting calibration of said at least one vital signs sensor in mitigation of thermal conditions in the vehicle.

10. The device of claim 8, further comprising a user interface for providing output, wherein said at least one processor being further configured for outputting via the user interface instructions to the passenger to perform at least one of extending a predetermined body portion out of the window and making accessible a predetermined inner cavity portion at a body orifice in mitigation of thermal conditions in the vehicle.

11. The device of claim 1, wherein said at least one imaging sensor comprising at least one thermal sensor configured for obtaining temperature data of at least the area confined by the window, wherein said at least one processor being further configured for analyzing said temperature data to recognize a pattern indicating usage of a climate control system of the vehicle.

12. The device of claim 11, wherein said at least one processor being further configured for determining and effecting calibration of said at least one vital signs sensor in compensation of a difference in the measurement of the health parameter caused by usage of the climate control system.

13. The device of claim 11, further comprising a user interface for providing output, wherein said at least one processor being further configured for outputting via the user interface instructions to the passenger to perform at least one of extending a predetermined body portion out of the window and making accessible a predetermined inner cavity portion at a body orifice in override of disruptive impact on the measurement of the health parameter caused by usage of the climate control system.

14. The device of claim 1, wherein said at least one processor being further configured for: analyzing said at least one image to determine a vibration frequency of the vehicle; and removing the vibration frequency from the measurement obtained by said at least one vital signs sensor.

15. The device of claim 1, further comprising a user interface for providing output, wherein said at least one processor being further configured for: analyzing said at least one image to determine a vibration frequency of the vehicle; and, responsive to determination that the vibration frequency exceeding a predetermined threshold, outputting via the user interface instructions to an operator of the vehicle to turn and maintain off the vehicle's engine for duration of the measurement.

16. The device of claim 1, further comprising a user interface for providing output, wherein said at least one processor being further configured for analyzing said at least one image to determine at least one of location and velocity of the vehicle and outputting via the user interface instructions to an operator of the vehicle to limit velocity and to halt the vehicle at a predetermined location.

17. The device of claim 1, wherein said at least one imaging sensor and said at least one vital signs sensor comprising at least one sensor selected from the group consisting of: a video camera; a thermal camera; a depth camera; an ultra-wideband radar; a laser speckle imaging device; a microphone; an ultrasonic sensor; a radiance sensor; and a laser Doppler vibrometer.

18. The device of claim 1, wherein the health parameter being selected from the group consisting of: a body temperature; a breathing rate; a breathing depth; a heart rate; a heart rate stability; cough presence; a blood oxygenation level; and a voice-indicated nasal congestion and/or throat irritation.

19. The device of claim 1, wherein said at least one processor being further configured for analyzing said at least one image to determine at least one personal parameter of the passenger selected from the group consisting of: age; gender; weight; height; and facial recognition.

20. The device of claim 1, wherein said at least one processor being further configured for: performing analysis of and extracting from said at least one image a unique identifier of the vehicle; and providing an output associating the unique identifier with the measurement obtained for each passenger of the vehicle.

21. A method for automated health check of passengers of a vehicle, comprising:
acquiring from at least one imaging sensor at least one image of at least an area confined by a window of the vehicle;
analyzing said at least one image to determine location of the window;
determining based on the determined location of the window a location of a passenger;
determining at least one vital signs sensor being oriented to a predetermined point of view in relation to the location of the passenger determined; and
obtaining a measurement of a health parameter of the passenger from said at least one vital signs sensor.

22. The method of claim 21, further comprising reorienting said at least one vital signs sensor to the predetermined point of view by at least one of a mechanical reorienting means and an electronical reorienting means.

23. The method of claim 21, further comprising instructing the passenger to move at least a body portion for placing said at least one vital signs sensor in orientation to the predetermined point of view.

24. The method of claim 21, further comprising: obtaining depth data of at least the area confined by the window from at least one spatial sensor comprised in said at least one imaging sensor; and analyzing said depth data to determine whether the window being in a rolled down position allowing clear line-of-sight between said at least one vital signs sensor and the passenger.

25. The method of claim 24, further comprising: prior to said obtaining the measurement and responsive to determination that the window being in position not allowing clear line-of-sight between said at least one vital signs sensor and the passenger, providing instructions to an operator of the vehicle to roll and maintain the window down for duration of the measurement.

26. The method of claim 21, further comprising: prior to said obtaining the measurement and responsive to determination that the location of the window exceeding a predetermined threshold distance in relation to said at least one vital signs sensor, determining a corrective translation of the vehicle relocating the window within the predetermined threshold distance; and providing instructions to an operator of the vehicle for effecting the corrective translation.

27. The method of claim 21, further comprising: obtaining temperature data of at least the area confined by the window from at least one thermal sensor comprised in said at least one imaging sensor, and analyzing said temperature data to determine whether thermal conditions in the vehicle enable proper functioning of said at least one vital signs sensor.

28. The method of claim 27, further comprising determining and effecting calibration of said at least one vital signs sensor in mitigation of thermal conditions in the vehicle.

29. The method of claim 27, further comprising outputting instructions to the passenger to perform at least one of extending a predetermined body portion out of the window and making accessible a predetermined inner cavity portion at a body orifice in mitigation of thermal conditions in the vehicle.

30. The method of claim 21, further comprising: obtaining temperature data of at least the area confined by the window from at least one thermal sensor comprised in said at least one imaging sensor, and analyzing said temperature data to recognize a pattern indicating usage of a climate control system of the vehicle.

31. The method of claim 30, further comprising: determining and effecting calibration of said at least one vital signs sensor in compensation of a difference in the measurement of the health parameter caused by usage of the climate control system.

32. The method of claim 30, further comprising: outputting instructions to the passenger to perform at least one of extending a predetermined body portion out of the window and making accessible a predetermined inner cavity portion at a body orifice in override of disruptive impact on the measurement of the health parameter caused by usage of the climate control system.

33. The method of claim 21, further comprising analyzing said at least one image to determine a vibration frequency of the vehicle; and removing the vibration frequency from the measurement obtained by said at least one vital signs sensor.

34. The method of claim 21, further comprising: analyzing said at least one image to determine a vibration frequency of the vehicle; and, responsive to determination that the vibration frequency exceeding a predetermined threshold, outputting instructions to an operator of the vehicle to turn and maintain off the vehicle's engine for duration of the measurement.

35. The method of claim 21, further comprising: analyzing said at least one image to determine at least one of location and velocity of the vehicle, and outputting instructions to an operator of the vehicle to limit velocity and to halt the vehicle at a predetermined location.

36. The method of claim 21, further comprising analyzing said at least one image to determine at least one personal parameter of the passenger selected from the group consisting of: age; gender; weight; height; and facial recognition.

37. The method of claim 21, further comprising: performing analysis of and extracting from said at least one image a unique identifier of the vehicle; and providing an output associating the unique identifier with the measurement obtained for each passenger of the vehicle.

\* \* \* \* \*